(12) United States Patent
Wilhelm (10) Patent No.: US 11,338,157 B2
(45) Date of Patent: May 24, 2022

(54) BREATHING BAG FOR A CLOSED-CIRCUIT RESPIRATOR AS WELL AS CLOSED-CIRCUIT RESPIRATOR

(71) Applicant: Dräger Safety AG & Co. KGaA, Lübeck (DE)

(72) Inventor: Christian Wilhelm, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 753 days.

(21) Appl. No.: 16/217,399

(22) Filed: Dec. 12, 2018

(65) Prior Publication Data

US 2019/0184211 A1 Jun. 20, 2019

(30) Foreign Application Priority Data

Dec. 14, 2017 (DE) .................. 10 2017 011 582.6

(51) Int. Cl.
*A61M 16/10* (2006.01)
*A62B 9/00* (2006.01)
*A62B 7/10* (2006.01)

(52) U.S. Cl.
CPC .............. *A62B 7/10* (2013.01); *A61M 16/105* (2013.01); *A62B 9/00* (2013.01)

(58) Field of Classification Search
CPC .... A62B 7/00; A62B 7/02; A62B 7/04; A62B 7/06; A62B 7/08; A62B 7/10; A62B 7/12; A62B 7/14; A61M 16/0045; A61M 16/0075; A61M 16/0078; A61M 16/0081; A61M 16/0084; A61M 16/009; A61M 16/0093; A61M 16/105; A61M 16/1055;
(Continued)

(56) References Cited

U.S. PATENT DOCUMENTS 4,252,114 A * 2/1981 Seres ...................... A62B 9/00
128/205.16
4,879,996 A * 11/1989 Harwood, Jr. ........... A62B 7/10
128/202.26
(Continued)

FOREIGN PATENT DOCUMENTS

CN 85108606 A 10/1986
CN 204543308 U 8/2015
(Continued)

OTHER PUBLICATIONS

English Machine Translation of DE102014017954B4 provided by Espacenet (Year: 2014).*
(Continued)

*Primary Examiner* — Joseph D. Boecker
*Assistant Examiner* — Brian T Khong
(74) *Attorney, Agent, or Firm* — McGlew and Tuttle, P.C.

(57) ABSTRACT

A breathing bag (1) for a closed-circuit respirator (100) has a bag component (2), which encloses an inner volume (3). The bag component (2) can reversibly assume at least one unfolded state (4) and a folded-in state (5). The bag component (2) encloses a larger inner volume (3) in the unfolded state (4) than in the folded-in state (5). Moreover, a closed-circuit respirator (100) is provided, having at least one counter-lung, a filter device, an oxygen source as well as a housing. The counter-lung, the filter device and the oxygen source are arranged in the housing.

22 Claims, 7 Drawing Sheets

(58) Field of Classification Search
CPC ............ A61M 16/106; A61M 16/1065; A61M 16/107; A61M 16/206; A61M 16/207; A61M 16/208; A61M 16/209; A61M 16/22; A61M 2016/0036; A61M 2016/0039; A61M 2016/0042
See application file for complete search history.

(56) References Cited

U.S. PATENT DOCUMENTS

| | | | | |
|---|---|---|---|---|
| 5,787,880 | A * | 8/1998 | Swanson | A61M 16/0084 128/202.28 |
| 6,443,149 | B1 * | 9/2002 | Wise | A62B 7/08 128/202.26 |
| 2006/0272644 | A1 * | 12/2006 | Halpern | A61M 16/0057 128/205.13 |
| 2008/0078386 | A1 * | 4/2008 | Feldhahn | A61M 16/16 128/204.18 |
| 2014/0318545 | A1 * | 10/2014 | Ackerman | A61M 16/208 128/205.14 |
| 2016/0199253 | A1 | 7/2016 | Di Capua et al. | |

FOREIGN PATENT DOCUMENTS

| | | | |
|---|---|---|---|
| CN | 105664390 A | 6/2016 | |
| DE | 37 42 639 A1 | 7/1988 | |
| DE | 103 42 011 B3 | 12/2004 | |
| DE | 10 2014 017 954 A1 | 6/2016 | |
| DE | 102014017954 A1 * | 6/2016 | ............... A62B 7/10 |
| DE | 10 2016 000 268 A1 | 7/2017 | |
| GB | 1136141 A | 12/1968 | |
| GB | 2054387 A * | 2/1981 | .......... A61M 16/205 |

OTHER PUBLICATIONS

Shanghai Medical Device Practical Manual; Sep. 30, 1989, Xue Boqing et al., Wen Jiang Publishing House, p. 763.
Packaging Container Structure Design and Manufacturing 2nd Edition, Jan. 31, 2016, Song Baofeng et al., Culture Development Press, p. 152.
Goal Mine Safety Instruments and Equipment; p. 245; Apr. 1, 1992; ISBN: 7-5020-0572-2/TD-527.
Modern Packaging Materials and Technology Applications, Practical Technical Textbook Compilation Group Guangdon Science and Technology Press, p. 263, Apr. 30, 2008.
Song Baofeng et al., Packaging Container Structure Design and Manufacturing, Culture Development Press, p. 224, Jan. 30, 2016.
Jiang Zhaojie et al., Primary Assembly Fitter Technology, Tianjin Science and Technology Press, p. 81, Jul. 31, 2017.

* cited by examiner

BREATHING BAG FOR A CLOSED-CIRCUIT RESPIRATOR AS WELL AS CLOSED-CIRCUIT RESPIRATOR

CROSS REFERENCE TO RELATED APPLICATIONS

This application claims the benefit of priority under 35 U.S.C. § 119 of German Application 10 2017 011 582.6, filed Dec. 14, 2017, the entire contents of which are incorporated herein by reference.

FIELD OF THE INVENTION

The present invention pertains to a breathing bag for a closed-circuit respirator, having a bag component, which encloses an inner volume, wherein the bag component can reversibly assume at least one unfolded state and a folded-in state, and wherein the bag component further encloses a larger inner volume in the unfolded state than in its folded-in state. Moreover, the present invention pertains to a closed-circuit respirator, having at least one counter-lung, a filter device, an oxygen source as well as a housing, wherein the counter-lung, the filter device and the oxygen source are arranged in the housing.

BACKGROUND OF THE INVENTION

Closed-circuit respirators are basically known and are often used under very difficult conditions in order to make it possible to provide an especially ambient air-independent supply of breathing air for a user of the closed-circuit respirator. Operating sites and operating conditions of closed-circuit respirators are, for example, in firefighting as part of the equipment of fire companies, but also in mine rescue. Prior-art closed-circuit respirators have as the central component a counter-lung with a breathing bag. Other components of closed-circuit respirators may be, for example, filter units, especially $CO_2$ filters, as well as air conditioning devices and an oxygen source.

The breathing bag of a closed-circuit respirator is usually used as a storage volume or an active gas reservoir of a user of the closed-circuit respirator for the exhaled air, from which the carbon dioxide had been removed. The uptake of a quantity of gas can be made possible especially due to an unfolding process or an inflation, and release of a quantity of gas from the breathing bag can analogously be made possible by folding in or collapsing. Tightness of the breathing bag, in particular, is decisive for the satisfactory functioning of a breathing bag and hence of the entire closed-circuit respirator. Breathing bags according to the state of the art are usually complicated constructions, for which individual components are made from a suitable material corresponding to a pattern and are subsequently connected to one another by connection in substance according to a welding process. These complicated, multistep processes for manufacturing a breathing bag according to the state of the art are especially time-consuming and labor-intensive and, moreover, cannot be automated. The consequence is the high cost of the manufacture of prior-art breathing bags. Moreover, tightness of the breathing bag is to be checked carefully at every individual connecting seam due to the prior-art breathing bag being fitted together from a pattern, so that the quality control and quality assurance of a finished breathing bag is also time-consuming and complicated.

SUMMARY OF THE INVENTION

Based on this state of the art, a basic object of the present invention is at least partially to eliminate these drawbacks of breathing bags for closed-circuit respirators as well as of closed-circuit respirators. The object of the present invention is therefore to provide a breathing bag for a closed-circuit respirator as well as a closed-circuit respirator, which simplify the manufacture of a breathing bag in as simple and cost-effective a manner as possible, and the breathing bag manufactured can at the same time have the simplest configuration possible as a whole and can be manufactured in an especially flexible manner especially in terms of its properties.

The above object is accomplished by a breathing bag for a closed-circuit respirator with the features according to the invention. Further, the object is accomplished by a closed-circuit respirator comprising at least one counter-lung, a filter device, an oxygen source, and a housing, wherein the counter-lung, the filter device and the oxygen source are arranged in the housing, wherein the counter-lung comprises a breathing bag with the features according to the invention. Features and details that are described in connection with the breathing bag according to the present invention are, of course, also applicable in connection with the closed-circuit respirator according to the present invention and vice versa, so that reference is and can always mutually be made to the individual aspects of the present invention concerning the disclosures.

According to a first aspect of the present invention, the object is accomplished by a breathing bag for a closed-circuit respirator, having a bag component, which encloses an inner volume, wherein the bag component can reversibly assume at least one unfolded state and a folded-in state, and wherein the bag component encloses a larger inner volume in its unfolded state than in its folded-in state. A breathing bag according to the present invention is characterized in that the bag component has a one-piece bag section and a one-piece tray section, wherein the bag section has at least essentially a higher flexibility than does the tray section, and wherein the bag section at least partially dips into the tray section at least in the folded-in state.

A breathing bag according to the present invention is intended for use in a closed-circuit respirator. In particular, a breathing bag according to the present invention may form a part of a counter-lung of the closed-circuit respirator. A breathing bag according to the present invention has for this purpose a bag component, which in turn encloses an inner volume. This inner volume represents a gas reservoir, which is arranged in the breathing circuit of a user of the closed-circuit respirator. By assuming a folded-in or unfolded state, this inner volume enclosed by the bag component may be provided in different sizes, and the inner volume may be larger, especially maximal, in its unfolded state, and the inner volume may be smaller and preferably minimal in its folded-in state in case of a folded-in bag component. The bag component may be reversibly transformed between the folded-in state and the unfolded state, so that a variable gas volume, especially a cyclically variable gas volume, can be provided by a breathing bag according to the present invention for the breathing circuit of a user of the closed-circuit respirator.

As an essential feature of the present invention, provisions are made in the breathing bag according to the present invention for the bag component of the breathing bag according to the present invention to have at least two sections; a bag section and a tray section. The bag component according to the present invention may especially preferably consist at least essentially of these two sections. The two sections are each made in one piece according to the present invention. In particular, provisions may be made in case of both the bag section and the tray section for these to be configured integrally without additional sealing lines. A globally more simple configuration of the breathing bag according to the present invention from essentially only two building sections can be provided in this manner.

In particular, the breathing bag according to the present invention has, on the whole, fewer sealing lines due to this configuration comprising the tray section and the bag section, so that the testing of the breathing bag according to the present invention for tightness after the manufacture can be simplified. The manufacture of at least the bag section and of the tray section can also be made simpler, especially also to the effect that such a manufacture can be made able to be automated. A markedly simpler and more rapid and hence also more cost-effective manufacture of a breathing bag according to the present invention can be made possible in this manner.

When a breathing bag according to the present invention is used in a closed-circuit respirator, as was described above, the inner volume is cyclically enlarged and reduced. This may be brought about by the bag component likewise oscillating cyclically between the bag component folded-in state and the bag component unfolded state. To make it possible to ensure this, the bag section has at least essentially a higher flexibility than the tray section. At least essentially can mean in the sense of the present invention, in particular, that, for example, the wall sections of the bag section, for example, those sections (wall sections) of the bag sections that are arranged adjacent to the tray section, are configured as flexible sections. It can be made possible in this manner that the bag section is folded together into itself during a transition from an unfolded state into a folded-in state of the bag component and dips at least partly into the tray section. In other words, provisions may preferably be made for the bag section to have, in at least some sections, a lower Shore hardness than the tray section. The tray section itself may advantageously be configured so as to be rigid such that the tray section will not, at least essentially, change a tray section shape during the transition from the unfolded state into the folded-in state of the bag component of the breathing bag according to the present invention. Provisions may also be made for the bag section to also have areas with a higher rigidity. Thus, a cover area of the bag section, which is located opposite the tray section, may also be configured with a higher rigidity, especially even with a rigidity comparable to the rigidity of the tray section. The cover are of the bag section may be sized somewhat smaller than the tray section, with wall areas of the bag section, which are more flexible, extending circumferentially about the cover area and the periphery of the tray section. To make it possible in an especially simple manner for the bag section to dip at least partially into the tray section, the tray section and the bag section may be configured as being complementary to one another, in which case the bag section may preferably be configured as being minimally smaller than the tray section.

In summary, it can be made possible by a breathing bag according to the present invention that this breathing bag can be manufactured in a simpler, more effective and less complicated manner than prior-art breathing bags according to the state of the art. Moreover, a more maintenance-friendly configuration of breathing bags requiring less maintenance can be made possible due to the reduction of the number of individual parts of the breathing bag according to the present invention compared to breathing bags according to the state of the art.

Provisions may also be made in case of a breathing bag according to the present invention for the bag section to have at least essentially a smaller wall thickness than the tray section. Provisions can be made in his manner in an especially simple manner for the bag section to have a higher flexibility than the tray section. At least essentially may mean in the sense of the present invention that the bag section does not globally have a smaller wall thickness than the tray section. It is, in particular, already sufficient in the sense of the present invention that the bag section has a smaller wall thickness than the tray section in the areas that are used or essential for the collapse of the bag section during the transition from the unfolded state into the folded-in state of the bag component of the breathing bag according to the present invention.

A breathing bag according to the present invention may also be configured such that the bag section and the tray section have different materials in at least some sections. It can be made possible in this manner in an especially simple manner that the tray section and the bag section possess different properties, especially in terms of the flexibility of the two sections. Especially preferred materials for manufacturing the bag section and the tray section are, for example, plastic materials and/or rubber materials. Thus, thermoplastic polyurethanes (TPU or TPE-U) may be used, for example, for the two sections. Depending on different polyurethanes, it is possible to provide especially more flexible and less flexible and/or even rigid configurations of the bag section and of the tray section. Other possible materials are ethylene-propylene-diene rubbers (EPDM). These rubbers can especially also be used in toxic environments, as a result of which the range of use of a breathing bag according to the present invention or of a closed-circuit respirator with such a breathing bag according to the present invention can be expanded.

Further, provisions may be made in a breathing bag according to the present invention for the bag section to have a mounting section, especially a circumferential mounting section, and for the tray section to have a counter-mounting section, especially a circumferential counter-mounting section, for connecting the bag section and the tray section in substance. It can be made possible in an especially simple manner due to such a mounting section and a counter-mounting section to connect the bag section and the tray section to one another in substance. Circumferential may mean in the sense of the present invention that the mounting section or the counter-mounting section is arranged along an edge of the respective section. Tightness of the entire bag component of the breathing bag can be ensured in an especially simple manner due to such a circumferential mounting section and counter-mounting section and the connection in substance of the bag section and of the tray section, which connection is carried out at these sections, can be brought about in an especially simple manner.

According to a variant of a breathing bag according to the present invention, provisions may furthermore be made for the bag section and the tray section to be bonded and/or welded to one another at the mounting section and at the counter-mounting section. Bonding and welding represent especially preferred embodiments of connections in substance for connecting a bag section or a tray section of a bag component of a breathing bag according to the present invention to one another in substance. It is possible to use in this connection especially welding in the embodiment of a breathing bag according to the present invention in which the bag section and/or the tray section are made of a thermoplastic polyurethane. Bonding has proved to be advantageous especially when the bag section or the tray section is made of an ethylene-propylene-diene rubber.

A breathing bag according to the present invention may be configured such that the bag section has a connection component and the tray section has a counter-connection component for the non-positive and/or positive-locking connection of the bag section to the tray section. Provisions may be made, in particular, in this alternative or additional embodiment for the bag section and the tray section not to be arranged irreversibly at one another, but for the inner volume to remain accessible, for example, for maintenance, by eliminating the non-positive and/or positive-locking connection of the bag section with the tray section even after the bag section has been mounted at the tray section to prepare the bag component. The connection components and counter-connection components used for this may be, for example, locking components, clip components and/or similar components. Provisions may, for example, also be made for connecting the tray section and the bag section of the bag component to one another both in substance and in a non-positive and/or positive-locking manner. Thus, one side may be connected in substance and the other three sides may be connected in a non-positive and/or positive-locking manner in case of a cuboid embodiment of the bag component and of the two sections. The side connected in substance may act in this case, for example, as a hinge for folding out the bag component for access to the inner volume of the bag component. Cleaning and/or disinfection of the inner volume of the bag component, for example, in the course of maintenance, can be made possible in this manner in an especially simple manner.

Further, provisions may also be made in a breathing bag according to the present invention for the bag section and/or the tray section to have a sealing component, especially a circumferential sealing component, for sealing the inner volume. Sealing of the inner volume can be made possible in an especially simple manner and especially with a high level of reliability by such a sealing component, which may be present at both the bag section and the tray section or even at both sections. The entry of gases from the outside into the inner volume or an uncontrolled discharge of the breathing gas from the inner volume to the outside can be prevented in this manner in an especially simple manner and with a high level of reliability.

Further, provisions may be made in a breathing bag according to the present invention for the bag section and/or the tray section to be manufactured in an injection molding process. Such an injection molding process represents an especially preferred manner of manufacture for providing a bag section or a tray section. In particular, both the bag section and the tray section may be manufactured in their final three-dimensional form by this injection molding process, as a result of which a subsequent assembly of, for example, a pattern for preparing a bottom section or tray section can be avoided. This manner of manufacture in an injection molding process can, moreover, especially also be automated in an especially simple manner, as a result of which the production of large quantities of the bag section and of the tray section can be made possible for a bag component of a breathing bag according to the present invention in an especially simple manner.

Provisions may furthermore be made according to an especially preferred variant of a breathing bag according to the present invention for the mounting section and/or the connection component and/or the sealing component to be manufactured together with the bag section in a multicomponent injection molding process, and/or for the counter-mounting section and/or the counter-connection component and/or the sealing component to be manufactured together with the tray section in a multicomponent injection molding process. Different requirements are usually imposed on the mounting section, the counter-mounting section, the connection component and the counter-connection component and/or the sealing component than on the tray section or the bag section. As an example, the connection component and/or the counter-connection component must be, for example, more stable and rigid for providing the non-positive and/or positive-locking connection between the bag section and the tray section than, for example, the flexible area of the bag section, which is used for folding in the bag section at the time of the transition from the unfolded state to the folded-in state of the bag component. A direct, especially monolithic manufacture of the respective component with the corresponding tray section or bag section can be provided by the use of a multicomponent injection molding process, in which a specially fitting material can be used for these individual components. Thus, the entire tray section or bag section can be manufactured together with the mounting section and/or counter-mounting section and/or connection component and/or counter-connection component and/or sealing component arranged at it, which possess the corresponding properties of the additional components, by selecting the materials used correspondingly by a single manufacturing operation in a multicomponent injection molding process.

Further, provisions may be made in case of a breathing bag according to the present invention for a surface of the bag section and/or of the tray section, which said surface faces the enclosing inner volume, to have a roughened configuration. Roughened in the sense of the present invention may mean especially that the surface has a slightly increased roughness. For example, adhesion of the surfaces of the bag section and of the tray section in case of a possible contact in the folded-in state can be avoided or at least made markedly difficult in this manner. A so-called lotus effect can also be provided by such a roughness of the surface, as a result of which the adhesion of dust or other impurities on the surface can be avoided or at least made markedly difficult. In particular, the removal of condensation water, which separates from the breathing air in the inner volume on the surface of the bag section and/or of the tray section, can also be facilitated especially well due to such a roughened surface.

Further, provisions may be made in a breathing bag according to the present invention for at least one tray junction area to be arranged at the tray section for one of the following components of the closed-circuit respirator:
  absorber unit,
  air conditioning unit,
  drainage unit,
  dispensing valve unit.

This list is, in particular, not complete, so that additional tray junction areas may also be provided, if technically meaningful and possible, at the wall section. Especially harmful gases, preferably $CO_2$, can be removed by an absorber unit from the breathing air in the inner volume of the breathing bag. An air conditioning unit makes possible the air conditioning, i.e., an increase or decrease in the temperature of the breathing air and, for example, additionally also the setting of the humidity of the breathing air in the inner volume of the breathing bag. Water condensed from the breathing air can be removed from the breathing bag by a drainage unit. Finally, a dispensing valve unit makes it possible to feed additional gas, especially oxygen, into the breathing volume, especially when the volume of the breathing bag drops below a minimal volume of the bag component of the breathing bag.

Further, a breathing bag according to the present invention may be improved such that the at least one junction area, especially the junction area for the dispensing valve unit, is configured as a pocket protruding into the inner volume. Such a pocket in the tray section is preferably an indentation into the inner volume of the bag component, which indentation is accessible from the outside. However, this pocket is separated from the inner volume, so that there is no connection between the inner volume and the pocket. It can be made possible in this manner, for example, to arrange the dispensing valve unit completely outside the inner volume at the bag component of a breathing bag according to the present invention. It can be made possible in this manner during a maintenance of the breathing bag that cleaning and/or disinfection of the valve unit is no longer absolutely necessary.

Further, provisions may be made in case of a breathing bag according to the present invention for at least one bag junction area to be arranged for a pressure relief valve at the bag section. Such a pressure relief valve may be especially a volume-controlled pressure relief valve. It is possible by means of such a pressure relief valve in the bag section especially to avoid an excessively high pressure in the bag component and hence in the entire closed-circuit breathing system. The breathing resistance of a user of a closed-circuit respirator can be regulated and/or limited in this manner with a breathing bag according to the present invention. In particular, a volume-controlled actuation of the pressure relief valve can be made possible in an especially simple manner by arranging the pressure relief valve in the bag section. Since the bag section is the decisive section, which moves and expands for assuming the unfolded state of the bag component, it is possible to ensure in an especially simple manner by arranging the pressure relief valve at the bag junction area of the bag section that triggering of the pressure relief valve is coupled with a position of the bag junction area, especially with a maximum position in the unfolded state, and with the especially maximum inner volume of the component, which inner volume is associated therewith.

A breathing bag according to the present invention may preferably be improved such that the bag junction area is configured as an area of the bag section with increased rigidity and has especially at least essentially a sleeve-like configuration. An especially good and secure arrangement of the pressure relief valve can be ensured in this manner by a bag junction area with increased rigidity, because an accidental or unintended removal of the pressure relief valve from the bag junction area, for example, due to excessively high flexibility in the area of the bag junction area, can be avoided hereby with certainty. In particular, snapping into and snapping out of the bag junction area can, for example, be made possible and/or further simplified by a sleeve-like configuration of the bag junction area in an especially simple manner.

Further, a breathing bag according to the present invention may be further improved such that a pressure relief valve is arranged at the junction area for the protection of the bag component against overpressure. The pressure relief valve has a valve body and a valve mechanism arranged in the valve body, the valve body having a fastening section for fastening to a counter-fastening section of the bag junction area in a fastening position, wherein the pressure relief valve is in a fluid-communicating contact (connection) with the inner volume in the fastening position. It can be made possible in this manner, in particular, to arrange the pressure relief valve directly at the bag section of the bag component of a breathing bag according to the present invention. The fastening section of the valve body of the pressure relief valve may be arranged for this purpose at the counter-fastening section of the bag junction area. For example, the fastening section may represent in the valve body a circumferential groove in the valve body in case of a sleeve-like bag junction area. The pressure relief valve can be arranged at the bag section or at the bag component in an especially simple manner in this manner by simply pressing or snapping the entire valve body into the bag junction area having a sleeve-like configuration. Provisions are made especially preferably, in particular, for the pressure relief valve to be connected directly to the breathing bag or the inner volume of the breathing bag in a fluid-communicating manner. The need for providing flexible tubes or lines between the bag component of the breathing bag and the pressure relief valve can be avoided in this manner. Simpler sealing, especially by avoiding sealing lines between the flexible tubes or lines and the bag component or the pressure relief valve, can be ensured in this manner.

Furthermore, a breathing bag according to the present invention may be improved such that the fastening section and/or the counter-fastening section have a sealing section for sealing the valve body against the bag junction area. Especially good sealing can be provided in this manner between the bag section and the pressure relief valve. An unintended or uncontrolled discharge or inflow of gases from the inner volume or into the inner volume can be reliably avoided in this manner.

As an alternative, a breathing bag according to the present invention may be improved such that the valve body is configured integrally with the bag junction area, especially in a multicomponent injection molding process. An even better sealing of the inner volume of the breathing bag can be provided in this manner in the area of the bag junction area, because no sealing line needs to be sealed between the valve body and the bag section. This can be made possible especially because the valve body is configured as an integral component of the bag section. It can furthermore be made possible by the use of a multicomponent injection molding process that the properties required for the valve body and the bag junction area, for example, in terms of flexibility or rigidity, can be ensured in an especially simple manner and with great variability.

A breathing bag according to the present invention may also be improved such that the valve body, and especially the valve mechanism, have a rotationally symmetrical or essentially rotationally symmetrical configuration. It can be made possible in this manner that the valve body or the entire pressure relief valve are configured such that they can be mounted in an especially simple manner. This can be made possible especially because a rotationally symmetrical pressure relief valve does not have a preferential direction in relation to its rotation axis, which direction would have to be taken into account during the mounting of the pressure relief valve on the bag junction area.

Further, provisions may be made in a breathing bag according to the present invention for the bag section to have a frame component for the positive-locking and/or non-positive arrangement of a breathing bag plate. Such a breathing bag plate is used, for example, to apply or maintain a certain pressure on the breathing gas in the inner volume of the bag component. Due to a frame component at the bag section, such a breathing bag plate can be fastened and/or arranged at the bag component of a breathing bag according to the present invention in an especially simple and reliable manner.

As an alternative, provisions may be made in a breathing bag according to the present invention for a breathing bag plate to be configured integrally with the bag section, especially for the breathing bag plate to be manufactured together with the bag section in a multicomponent injection molding process. Provisions are made, in particular, in this additional improvement of a breathing bag according to the present invention for the breathing bag plate to be manufactured as an integral component of the bag section. A multicomponent injection molding process can preferably be used for this, as a result of which the required properties of the breathing bag plate and of the rest of the bag section can be provided as components in an especially simple manner and especially in a single manufacturing step during the injection molding by the use of respective suitable materials.

A breathing bag according to the present invention may especially preferably be configured such that the bag component has essentially one of the following shapes:
cuboid
bar
double bar
cylinder
lens
sphere.

This list is, in particular, not complete, so that a breathing bag according to the present invention or the bag component of a breathing bag according to the present invention may also have other shapes insofar as technically meaningful and possible.

According to a second aspect of the present invention, the object is accomplished by a closed-circuit respirator, having at least a counter-lung, a filter device, an oxygen source as well as a housing, wherein the counter-lung, the filter device and the oxygen source are arranged in the housing. A closed-circuit respirator according to the present invention is characterized in that the counter-lung has a breathing bag according to the first aspect of the present invention. All the advantages that are described in detail in reference to a breathing bag according to the first aspect of the present invention can thus also be provided by a closed-circuit respirator according to the second aspect of the present invention, whose counter-lung has a breathing bag according to the first aspect of the present invention.

Further measures improving the present invention appear from the following description of exemplary embodiments of the present invention, which are shown in the figures. All the features and/or advantages appearing from the claims, the description and the drawings, including structural details and arrangements in space, may be essential for the present invention both in themselves and in the different combinations. Components having the same function and mode of action are designated by the same reference numbers in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
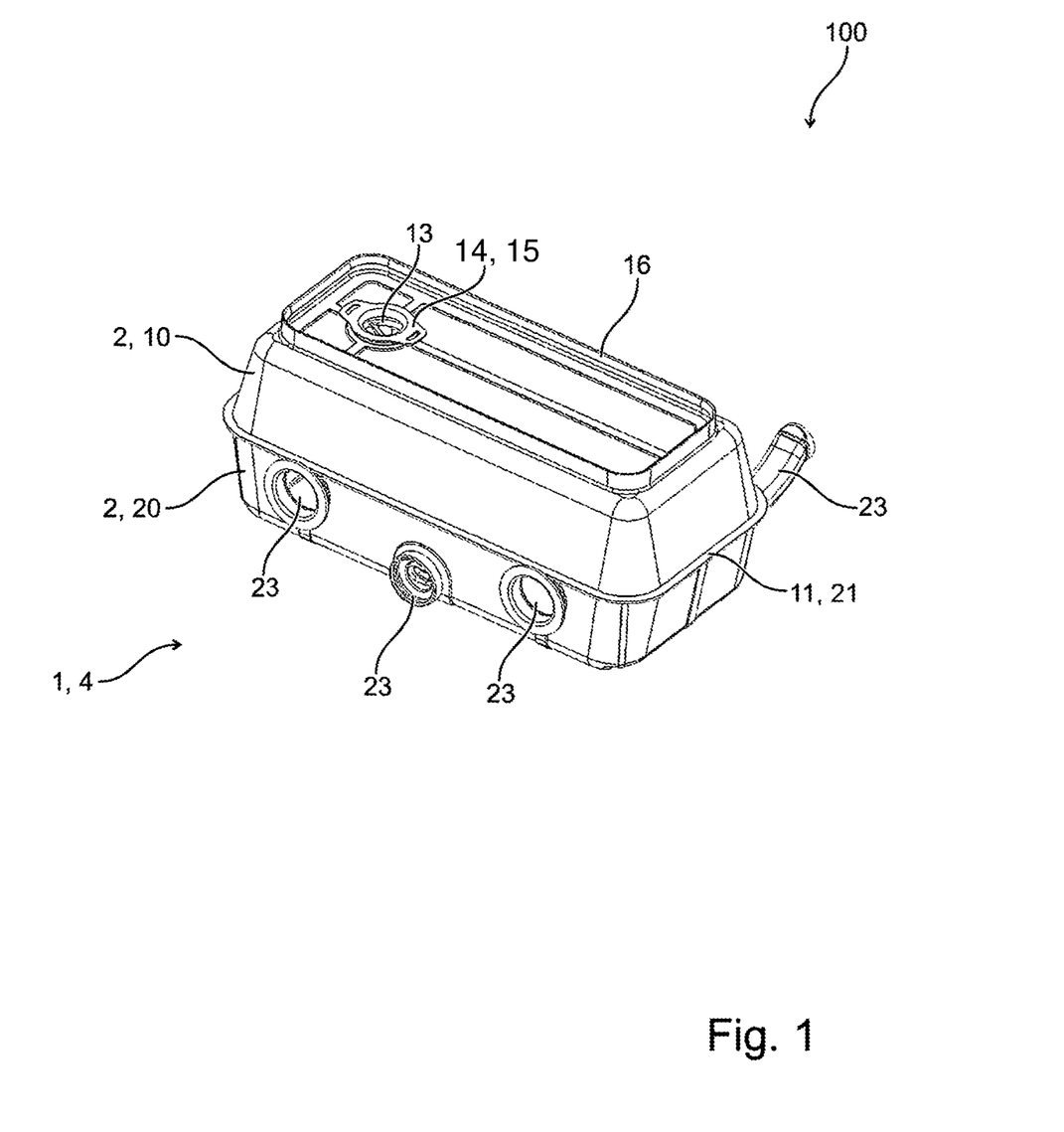
FIG. 1 is a perspective view showing a breathing bag according to the present invention of a closed-circuit respirator according to the present invention.

Referring to the drawings, FIG. 1 shows a breathing bag 1 according to the present invention of a closed-circuit respirator 100 according to the present invention. The closed-circuit respirator 100 comprises at least one counter-lung 114 (comprising the breathing bag 1), a filter device 110, an oxygen source 112, and a housing 120. The counter-lung 114, the filter device 110 and the oxygen source 112 are arranged in the housing 120. The counter-lung 114, comprised of the breathing bag 1, is shown, in particular, in its unfolded state 4, in which an inner volume 3 of the breathing bag 1 is especially large, especially having its maximum. As an essential feature of the present invention, a breathing bag 1 according to the present invention has a bag component 2, which is, in turn, built from a bag section 10 and a tray section 20. The bag component 2 may especially preferably comprise the bag section 10 and the tray section 20. In the embodiment shown, the bag section 10 and the tray section 20 are connected, especially bonded and/or welded, to one another in substance at a mounting section 11 and at a counter-mounting section 21. To ensure the functionality of the breathing bag 1, the bag component 2 may also assume, in addition to the unfolded state 4 shown, a folded-in state 5 (FIG. 4), in which the bag section 10 dips at least partially into the tray section 20. The bag section 10 has for this purpose, in at least some sections, a higher flexibility than the tray section 20. Provisions may preferably even be made for the tray section 20 to have a rigid configuration per se and not to change or essentially not to change a tray section shape during the transition from the unfolded state 4 into the folded-in state 5. This also makes it possible or easier, for example, to arrange in the tray section 20 a plurality of tray junction areas 23, which may be provided, for example, for absorber units, air conditioning units, drainage units and/or dispensing valves. The higher flexibility of the bag section 10 may be made possible, for example, by a smaller wall thickness of the bag section 10 compared to the tray section 20 or, as an alternative or in addition, also by correspondingly selecting a different material for the bag section 10 and for the tray section 20. Further, the bag section 10 may have a bag junction area 13, which may have, as is shown, a counter-fastening section 14 as well as a sealing section 15 for the arrangement of a pressure relief valve 40 (not shown). Moreover, a frame component 16 may be provided as an integral part at the bag (cover) section 10 for arranging a breathing bag plate 6 (not shown with this embodiment). In particular, an injection molding process proved to be advantageous for manufacturing the tray section 20 and the bag section 10 as molded parts/portions. In particular, a three-dimensional shape of the bag section 10 and of the tray section 20 can be prepared in this manner in an especially simple manner in a single manufacturing step. Providing a pattern in a complicated manner subsequently connecting it in substance to obtain a three-dimensional shape can be avoided in this way in an especially simple manner. Moreover, the injection molding process may be configured as a multicomponent injection molding process, as a result of which the properties needed in the different areas can be made possible in an especially simple manner, in particular, for example, for special areas of the bag section 10 and of the tray section 20, for example, the mounting section 11, the counter-mounting section 21 or the tray junction areas 23 and the bag junction area 13 by suitably selecting the materials used.

Figure 2:
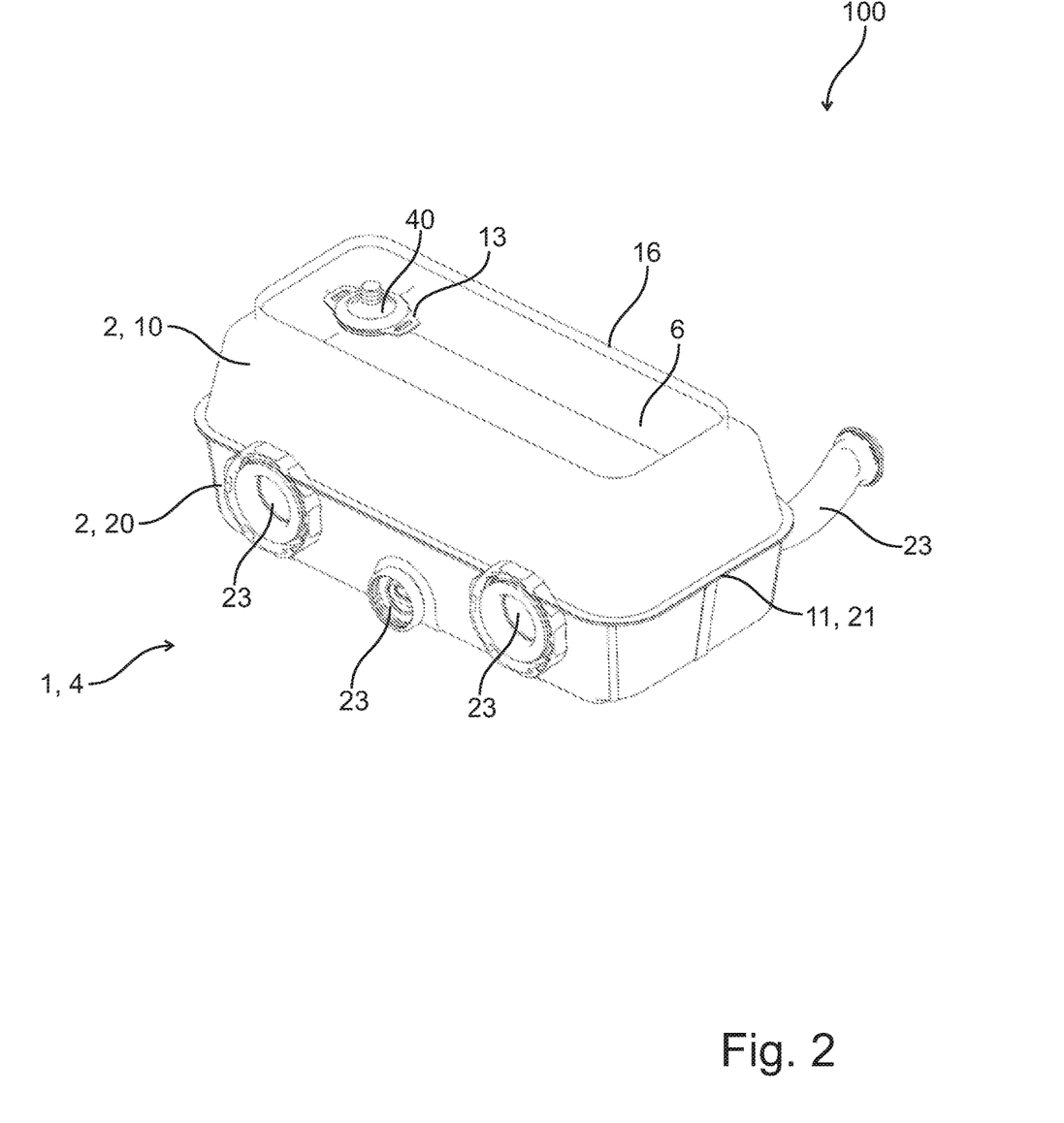
FIG. 2 is a perspective view showing another breathing bag according to the present invention of a respirator according to the present invention.

FIG. 2 shows the bag component 2 of the breathing bag 1, as is shown in FIG. 1, with connection sleeves being additionally arranged here at the tray junction areas 23. Moreover, the breathing bag plate 6 is arranged at the frame component 16 of the bag section 10, and the pressure relief valve 40 is inserted into the bag junction area 13. As is shown, the pressure relief valve 40 may have, at least essentially, for example, especially the valve body 41 (not shown) of the pressure relief valve 40, a rotationally symmetrical configuration, as a result of which the arrangement of the pressure relief valve 40 in the bag junction area 13 can be facilitated. Reference is made to FIG. 1 concerning the other properties and details of the breathing bag 1 shown.

Figure 3:
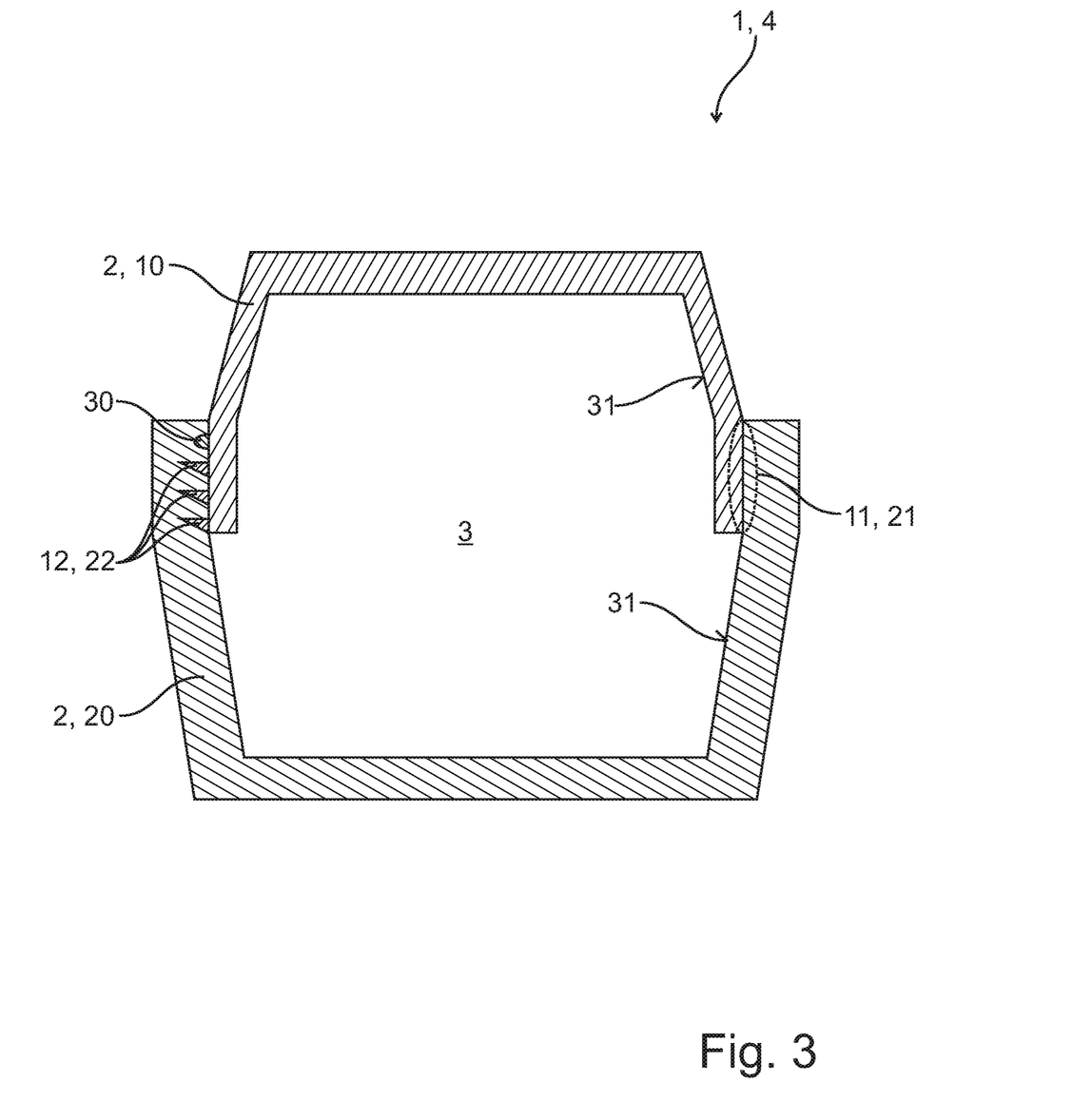
FIG. 3 is a schematic cross sectional view showing a breathing bag according to the present invention in an unfolded state.
Figure 4:
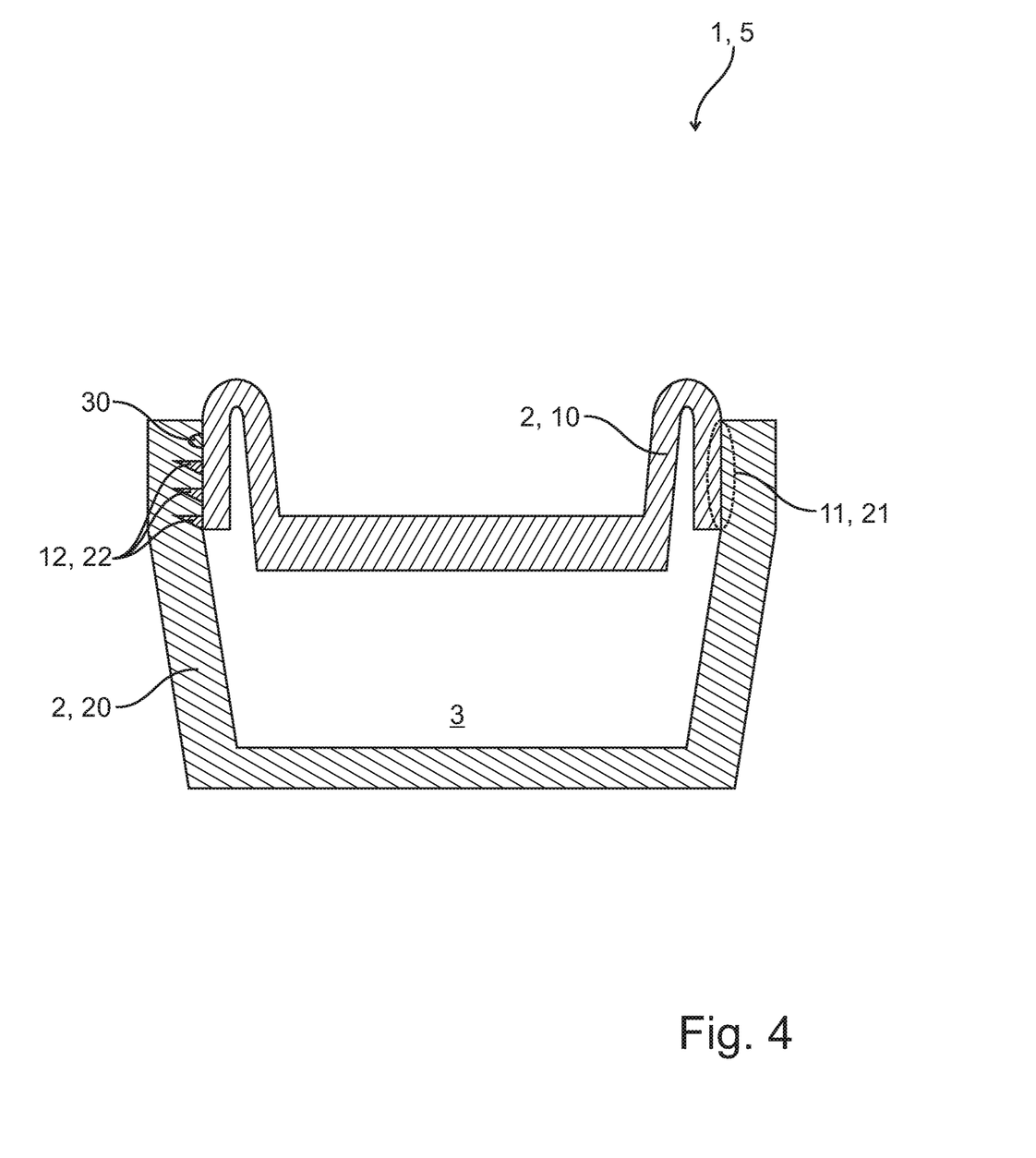
FIG. 4 is a schematic cross sectional view showing a breathing bag according to the present invention in a folded-in state.

FIGS. 3 and 4 show a schematic sectional view of a breathing bag 1 according to the present invention, the unfolded state 4 thereof being shown in FIG. 3 and the folded-in state 5 thereof being shown in FIG. 5. The two figures will therefore be described together below, and the details will always be discussed separately. The bag component 2 of the breathing bag 1 according to the present invention shown has, in turn, a bag section 10 and a tray section 20. It is already clearly visible here that, at least in some sections, the bag section 10 has a smaller wall thickness than the tray section 20. The higher flexibility of the bag section 10 compared to the tray section 20 can be provided in this manner in an especially simple manner. The inner volume 3 enclosed by the bag component 2 is likewise shown, and it can be seen in the comparison of FIGS. 3 and 4 that the inner volume 3 enclosed in the unfolded state 4 is larger than the inner volume 3 enclosed in the folded-in state 5. A mounting section 10 and a counter-mounting section 21, in which the bag section 10 and the tray section 20 are connected, especially bonded and/or welded, to one another in substance, are shown on the right-hand side. Connection components 12 and counter-connection components 22, which can provide a non-positive connection or connection in substance of the tray section 20 and the bag section 10 as parts of the bag section 10 and of the tray section 20, can be seen on the opposite-left-hand side. A locking connection is schematically embodied in this embodiment shown. Moreover, a sealing component 30, by which the tightness of the inner volume 3 of the bag component 2 of the breathing bag 1 according to the present invention can be increased, is shown adjacent to this. It can be ensured, in particular, by the non-positive and/or positive-locking connection of the tray section 20 and the bag section 10 by the connection components 12 and the counter-connection components 22, respectively, that, for example, the inner volume 3 of the bag component 2 remains accessible, for example, for maintenance procedures. Moreover, a surface 31 of the bag section 10 and of the tray section 20, which faces the inner volume 3, is shown at least in FIG. 3. The surfaces are shown without reference numbers in FIG. 4 for the sake of clarity. According to the present invention, this surface 31 may be provided as a roughened surface in order to prevent, for example, adhesion of the bag section 10 to the tray section 20 especially in the folded-in state 5. A so-called lotus effect may also be provided by such roughness to avoid the adhesion of dust and/or impurities and/or condensation water. FIGS. 3 and 4 differ from each other especially in that the bag component 2 is shown in the unfolded state in FIG. 3 and in the folded-in state in FIG. 4. It is clearly seen that only the bag section 10 will change a bag section shape during this transition from the unfolded state 4 to the folded-in state 5. This can be ensured especially by the bag section 10 having a higher flexibility, due, for example, to a smaller wall thickness, than the tray section 20.

Figure 5:
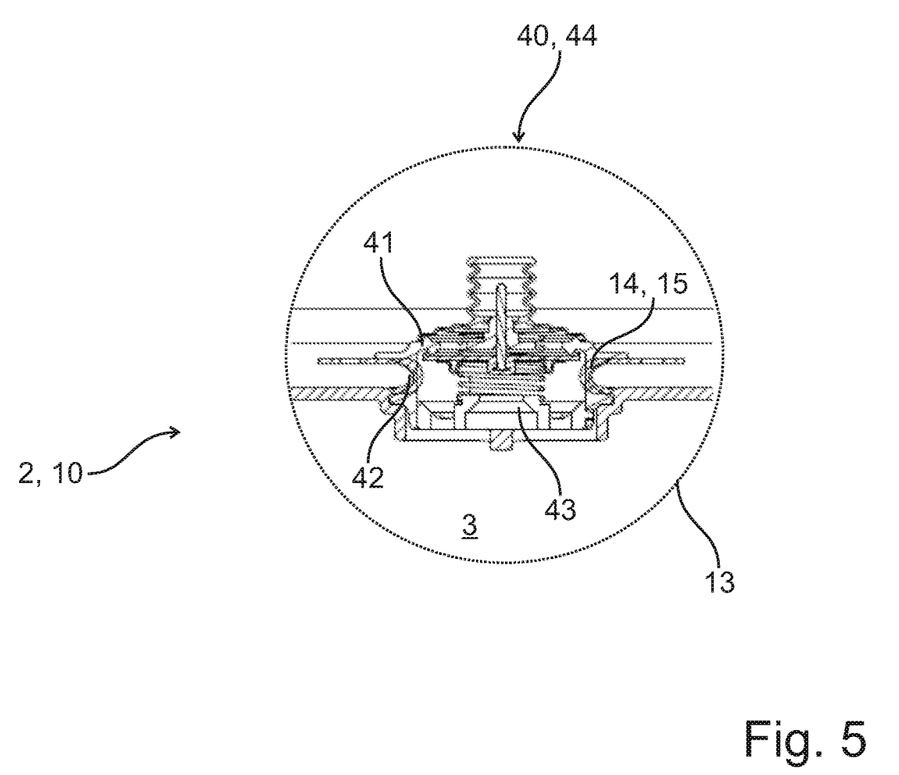
FIG. 5 is a cross sectional view showing a breathing bag junction area with a pressure relief valve.

A bag junction area 13 in the bag section 10 of a bag component 2 is shown in FIG. 5 in a sectional view, and a pressure relief valve 40 is arranged in its fastened position in this bag junction area 13. It is clearly seen that the bag junction area 13 has a sleeve-like (sleeve) configuration, as a result of which the counter-fastening section 14 can mesh with a groove-like (groove configuration) fastening section 42 of the valve body 41 in an especially simple manner. At the same time, a sealing section 15 may likewise mesh as a part of the counter-fastening section 14 with the groove configuration fastening section 42 in order to make it possible to ensure an especially reliable sealing of the bag junction area 13. The valve mechanism 43 or the valve body 41 of the pressure relief valve 40 is arranged according to the present invention such that it is connected to the inner volume 3 in a fluid-communicating manner. Direct arrangement of the pressure relief valve at the bag section 10 can be made possible in this manner. As an alternative, provisions may be made for the valve body 41 to be configured integrally with the bag section 10, especially with the bag junction area 13. An even better sealing of the entire bag component 2 can be achieved in this manner.

Figure 6:
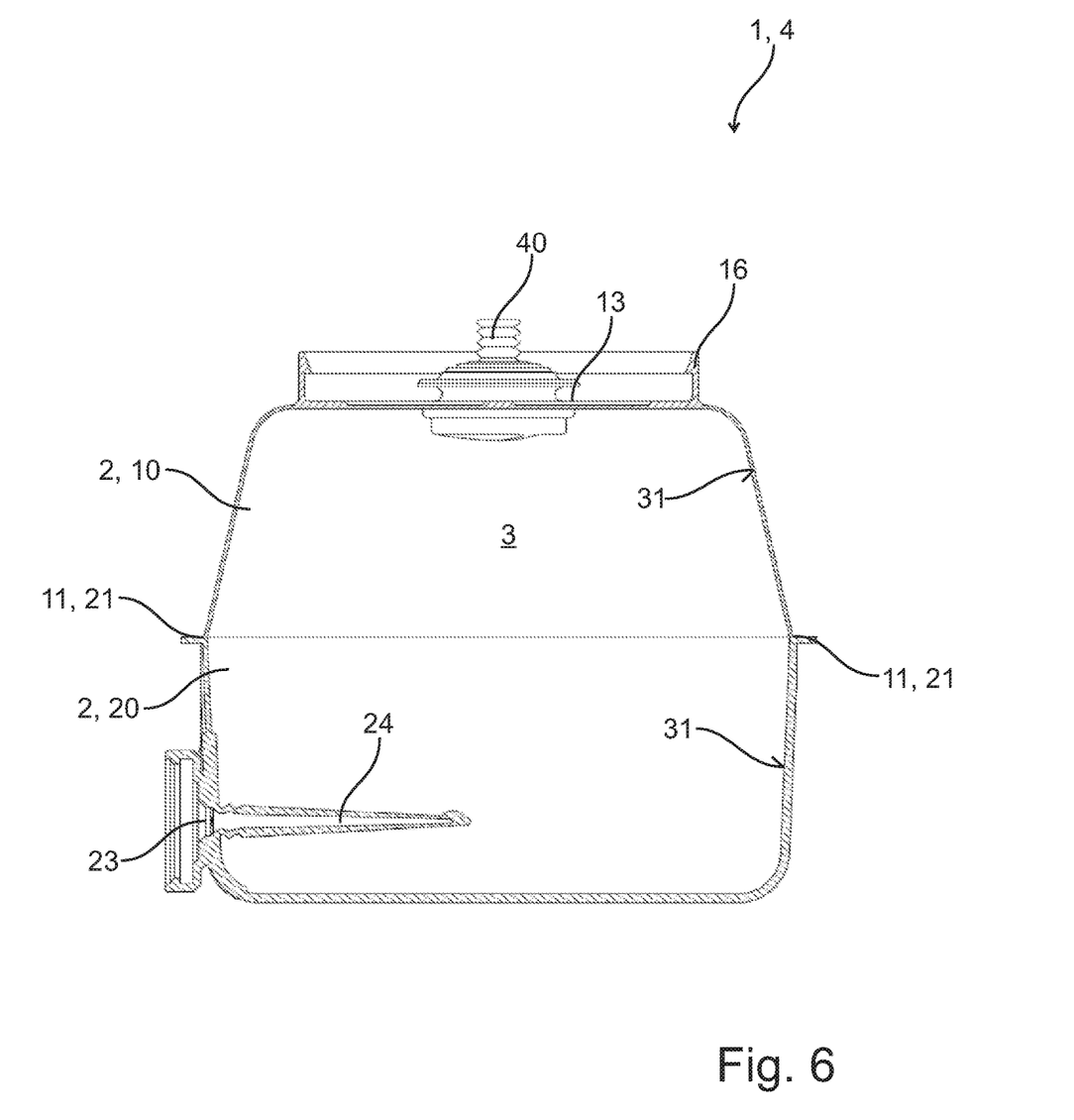
FIG. 6 is a cross sectional view showing another breathing bag according to the present invention.
Figure 7:
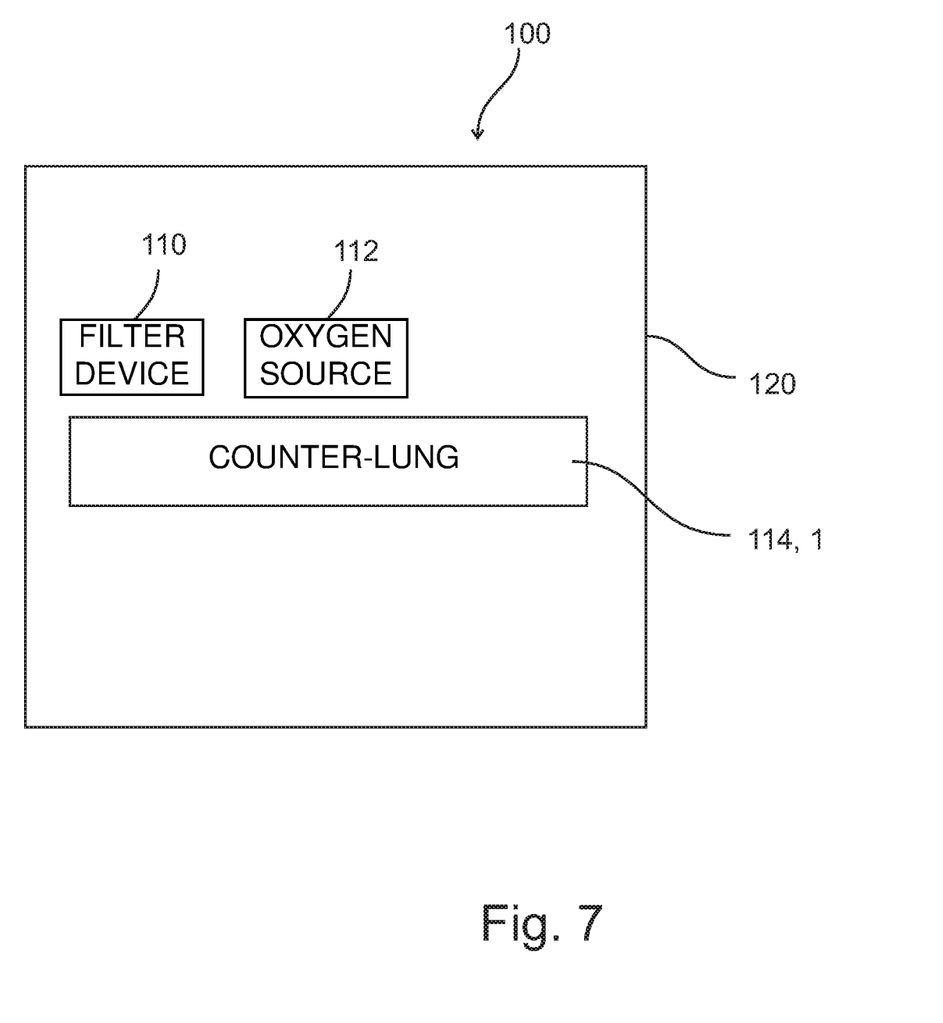
FIG. 7 is a schematic view of the closed circuit respirator.

FIG. 6 shows another sectional view of a breathing bag 1 according to the present invention in the unfolded state 4 thereof. In addition to the pressure relief valve 40, which is already described in FIG. 5 and which is likewise shown in its fastening position 44 in the bag junction area 13 here, FIG. 6 shows especially a tray junction area 23, which is configured as a pocket 24. This pocket 24 protrudes as an indentation into the inner volume 3 of the bag component 2, and the pocket 24 remains accessible from the outside of the bag component 2, but it has no direct connection to the inner volume 3. A component arranged in the pocket 24, for example, an actuating lever of a dispensing valve unit, can thus be deflected without direct contact with the inner volume 3. By avoiding a direct contact of the dispensing valve unit with the inner volume 3, it can be made possible that cleaning or disinfection of the dispensing valve unit is not absolutely necessary any longer. Moreover, the bag section 10 and the tray section 20, which have, in turn, a respective surface 31 and are connected to one another at mounting sections 11 and counter-mounting sections 21, are shown here as well. The frame component 16 is also shown in FIG. 6 as a part of the bag section 10.

While specific embodiments of the invention have been shown and described in detail to illustrate the application of the principles of the invention, it will be understood that the invention may be embodied otherwise without departing from such principles.

APPENDIX

List of Reference Numbers

1 Breathing bag
2 Bag component
3 Inner volume
4 Unfolded state
5 Folded-in state
6 Breathing bag plate
10 Bag section
11 Mounting section
12 Connection component
13 Bag junction area
14 Counter-fastening section
15 Sealing section
16 Frame component
20 Tray section
21 Counter-mounting section
22 Counter-connection component
23 Tray junction area
24 Pocket
30 Sealing component
31 Surface
40 Pressure relief valve
41 Valve body
42 Fastening section
43 Valve mechanism
44 Fastening position
100 Closed-circuit respirator
110 filter device
112 oxygen source
114 counter-lung
120 housing

What is claimed is:

1. A breathing bag for a closed-circuit respirator, the breathing bag having a bag section and a tray section formed by the process steps of:
   multi-component injection molding together a material of the bag section to form the bag section and a material of the tray section to form the tray section, the multi-component injection molding forming the breathing bag in one piece, the multi-component injection molding being performed to form a connection in substance between a mounting section of the bag section and a counter-mounting section of the tray section, the material of the bag section and the material of the tray section being different;
   the breathing bag being configured to enclose an inner volume, the breathing bag reversibly having an unfolded state and a folded-in state, the breathing bag enclosing a larger inner volume in the unfolded state than in the folded-in state,
   the bag section having a bag section flexibility that is higher than a tray section flexibility of the tray section, the bag section being configured to be arranged at least partially in the tray section in the folded-in state.

2. A breathing bag in accordance with claim 1, wherein the bag section has a smaller wall thickness than the tray section.

3. A breathing bag in accordance with claim 1, wherein:
   the bag section comprises a connection component; and
   the tray section comprises a counter-connection component for a non-positive locking connection and/or a positive locking connection, the non-positive and/or positive locking connection comprising a reversible and detachable connection, of the bag section to the tray section.

4. A breathing bag in accordance with claim 1, wherein the bag section and/or the tray section have a circumferential sealing component sealing the inner volume from an exterior environment of the breathing bag;
   the multi-component injection molding step including multi-component injection molding together a material of the circumferential sealing component and the material of the respective bag section or tray section, to form the entire respective bag section or tray section, the multi-component injection molding being performed to form a connection in substance between the material of the circumferential sealing component and the material of the respective bag section or tray section.

5. A breathing bag in accordance with claim 1, wherein a surface of the bag section and/or a surface of the tray section has a roughened configuration, the surface of the bag section and/or the surface of the tray section faces the enclosed inner volume.

6. A breathing bag in accordance with claim 1, wherein at least one tray junction area is arranged at the tray section for one of the following components of the closed-circuit respirator:
   absorber unit;
   air conditioning unit;
   drainage unit;
   dispensing valve unit.

7. A breathing bag in accordance with claim 6, wherein the at least one junction area comprises the junction area for the dispensing valve unit and is configured as a pocket protruding into the inner volume.

8. A breathing bag in accordance with claim 1, wherein the bag section is configured with at least one bag junction area for a pressure relief valve.

9. A breathing bag in accordance with claim 8, wherein the bag junction area is configured as an area of the bag section with increased rigidity and comprises a sleeve configuration.

10. A breathing bag in accordance with claim 9, further comprising a pressure relief valve arranged at the bag junction area for protection of the breathing bag against overpressure, said pressure relief valve being arranged to be exposed to the external environment, said pressure relief valve comprising:
   a valve body; and
   a valve mechanism arranged in the valve body, wherein:
   the valve body has a fastening section for fastening on a counter-fastening section of the bag junction area in a fastening position; and
   the pressure relief valve is in fluid-communicating connection with the inner volume in the fastening position.

11. A breathing bag in accordance with claim 10, wherein the fastening section and/or the counter-fastening section fastening section comprise a sealing section for sealing the valve body against the junction area.

12. A breathing bag in accordance with claim 10, wherein the valve body is injection molded and is configured integrally with the bag junction area and is formed in the multicomponent injection molding process, the multicomponent injection molding process connecting in substance a material of the valve body and the material of the bag section.

13. A breathing bag in accordance with claim 10, wherein the valve body and the valve mechanism have a rotationally symmetrical configuration.

14. A breathing bag in accordance with claim 1, wherein the bag section further comprises a frame component for a positive-locking and/or non-positive locking arrangement of a breathing bag plate.

15. A breathing bag in accordance with claim 1, wherein a breathing bag plate is multicomponent injection molded and configured integrally with the bag section and is manufactured together with the bag section in the multicomponent injection molding process, the multicomponent injection molding process connecting in substance a material of the breathing bag plate and the material of the bag section.

16. A breathing bag in accordance with claim 1, wherein the breathing bag has one of the following shapes:
cuboid;
bar;
cylinder;
sphere.

17. A breathing bag in accordance with claim 1, wherein:
the bag section is configured to move into the tray section from the unfolded state to the folded-in state without a use of external springs.

18. A breathing bag in accordance with claim 1, wherein:
the bag section has a mounting section and a connection component,
the multi-component injection molding step includes multi-component injection molding together a material of the mounting section, a material of the connection component, and the material of the bag section, to form the entire bag section;
the multi-component injection molding being performed to form a connection in substance between the material of the mounting section and the material of the bag section;
the multi-component injection molding being performed to form a connection in substance between the material of the connection component and the material of the bag section;
the material of the mounting section and the material of the bag section being different;
the material of the connection component, and the material of the bag section being different.

19. A breathing bag in accordance with claim 18, wherein:
the tray section has a counter-mounting section and a counter-connection component,
the multi-component injection molding step includes multi-component injection molding together a material of the counter-mounting section, a material of the counter-connection component, and the material of the tray section, to form the entire tray section;
the multi-component injection molding being performed to form a connection in substance between the material of the counter-mounting section and the material of the tray section;
the multi-component injection molding being performed to form a connection in substance between the material of the counter-connection component and the material of the tray section;
the material of the counter-mounting section and the material of the tray section being different;
the material of the counter-connection component, and the material of the tray section being different.

20. A breathing bag in accordance with claim 1, wherein:
the tray section has a counter-mounting section and a counter-connection component,
the multi-component injection molding step includes multi-component injection molding together a material of the counter-mounting section, a material of the counter-connection component, and the material of the tray section, to form the entire tray section;
the multi-component injection molding being performed to form a connection in substance between the material of the counter-mounting section and the material of the tray section;
the multi-component injection molding being performed to form a connection in substance between the material of the counter-connection component and the material of the tray section;
the material of the counter-mounting section and the material of the tray section being different;
the material of the counter-connection component, and the material of the tray section being different.

21. A breathing bag for a closed-circuit respirator, the breathing bag having a tray section and a bag section with a mounting section and a connection component, the bag section being formed by the process steps of:
multi-component injection molding together a material of the mounting section, a material of the connection component, and a material of a remaining portion of the bag section, to form the entire bag section;
the multi-component injection molding being performed to form a connection in substance between the material of the mounting section and the material of the remaining portion of the bag section;
the multi-component injection molding being performed to form a connection in substance between the material of the connection component and the material of the remaining portion of the bag section;
the material of the mounting section and the material of the remaining portion of the bag section being different;
the material of the connection component, and the material of the remaining portion of the bag section being different;
the breathing bag being configured to enclose an inner volume, the breathing bag reversibly having an unfolded state and a folded-in state, the breathing bag enclosing a larger inner volume in the unfolded state than in the folded-in state,
the bag section having a bag section flexibility that is higher than a tray section flexibility of the tray section, the bag section being configured to be arranged at least partially in the tray section in the folded-in state.

22. A breathing bag for a closed-circuit respirator, the breathing bag having a bag section and a tray section with a counter-mounting section and a counter-connection component, the tray section being formed by the process steps of:
multi-component injection molding together a material of the counter-mounting section, a material of the counter-connection component, and a material of a remaining portion of the tray section, to form the entire tray section;
the multi-component injection molding being performed to form a connection in substance between the material of the counter-mounting section and the material of the remaining portion of the tray section;
the multi-component injection molding being performed to form a connection in substance between the material of the counter-connection component and the material of the remaining portion of the tray section;

the material of the counter-mounting section and the material of the remaining portion of the tray section being different;

the material of the counter-connection component, and the material of the remaining portion of the tray section being different;

the breathing bag being configured to enclose an inner volume, the breathing bag reversibly having an unfolded state and a folded-in state, the breathing bag enclosing a larger inner volume in the unfolded state than in the folded-in state, the bag section having a bag section flexibility that is higher than a tray section flexibility of the tray section, the bag section being configured to be arranged at least partially in the tray section in the folded-in state.

* * * * *